United States Patent [19]
Hernandez

[11] Patent Number: 5,228,969
[45] Date of Patent: Jul. 20, 1993

[54] CAPILLARY ELECTROPHORESIS APPARATUS INCLUDING A CAPILLARY TUBE HAVING AN INCORPORATED OPTICAL DEVICE

[75] Inventor: Luis Hernandez, Toulouse, France

[73] Assignee: Europhor SA, Toulouse, France

[21] Appl. No.: 540,335

[22] Filed: Jun. 19, 1990

[30] Foreign Application Priority Data

Jun. 21, 1989 [FR] France .................. 89 08257

[51] Int. Cl.$^5$ .................. G01N 27/26; G01N 27/447
[52] U.S. Cl. .................. 204/299 R; 204/180.1
[58] Field of Search .................. 204/180.1, 299 R

[56] References Cited

U.S. PATENT DOCUMENTS 4,816,123  3/1989  Ogan et al. .................. 204/299 R X Primary Examiner—John Niebling
Assistant Examiner—John S. Starsiak, Jr.
Attorney, Agent, or Firm—Gottlieb, Rackman & Reisman

[57] ABSTRACT

A capillary electrophoresis apparatus with detection by fluorescence including an optical device incorporated in the capillary tube at the region of with the fluorescence detection zone. Depending on the angle of observation of the light emitted by fluorescence, the device is either a reflector or a color cut-off filter. The device may be incorporated on the outside surface of the capillary tube.

6 Claims, 1 Drawing Sheet

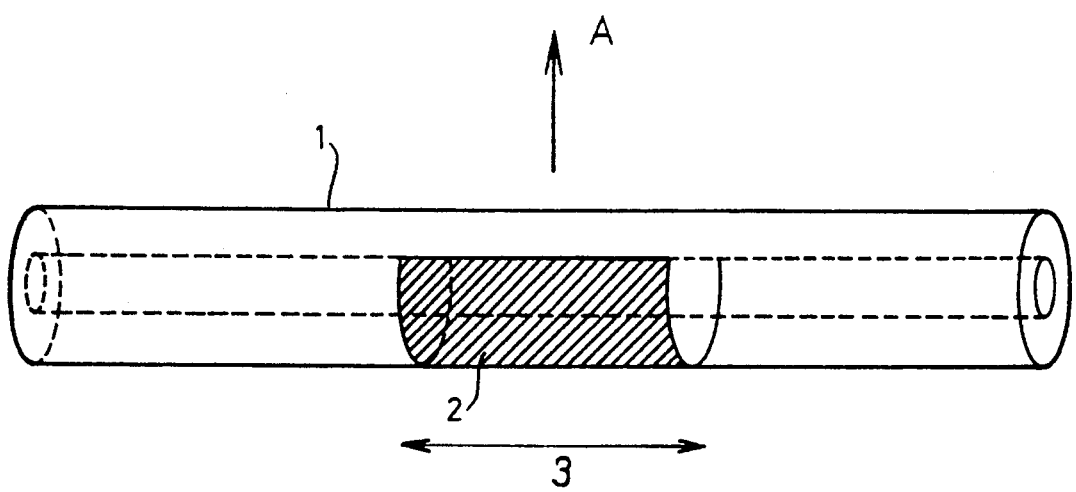

CAPILLARY ELECTROPHORESIS APPARATUS INCLUDING A CAPILLARY TUBE HAVING AN INCORPORATED OPTICAL DEVICE

The invention relates to a capillary electrophoresis apparatus including a capillary tube having an incorporated optical device.

BACKGROUND OF THE INVENTION

Capillary electrophoresis is a powerful separation technique making it possible to detect the presence of substances in detection zones of very small volume. This electrophoresis technique is particularly advantageous for application in the medical and biological field, with electrophoretic migration taking place either in a buffer or else on a gel.

Several detection modes (UV spectrometry, amperometry, . . .) may be used, but detection by fluorescence has been found to be particularly sensitive. See, for example, U.S. Pat. No. 4,675,300 issued Jun. 23, 1987, the disclosure of which is incorporated herein as background material by this reference. Fluorescence is the property possessed by certain substances whereby, when they are excited by light at a certain wavelength, they emit radiation at a wavelength longer than that of the incident rays.

The sensitivity of fluorescence detection comes from the fact that background emission (when not fluorescing) is practically nil so that large changes in emission are observed. This is in contrast to the conventional absorption phenomenon where the difference between the incident radiation and the emitted radiation is very small. In addition, selectivity is high due to the fact that two wavelengths are chosen (excitation energy and emission energy): this very precise choice makes very high selectivity possible.

In conventional fluorescence detectors, the light emitted by fluorescence is generally picked up either in the plane of the incident rays, or else (as taught by U.S. Pat. No. 4,675,300) perpendicularly to the plane of the incident rays.

Because of the tiny quantities of substances present, the amount of light emitted is low and it is necessary to provide optical devices either for separating the incident light from the emitted light, or else for reflecting the emitted light in a particular direction.

Such additional devices make it necessary to observe the light at a certain distance from the capillary, thus giving rise to a loss of sensitivity.

SUMMARY OF THE INVENTION

In order to mitigate this drawback, the invention provides a solution which consists in incorporating the optical device in the capillary tube of the apparatus.

Fluorescence may be observed in the incident light plane beyond the capillary tube, and in this case the optical device is a color cut-off filter which allows light to pass only at wavelengths that are longer than the wavelength of the incident light.

Fluorescence may also be observed in the incident light plane, but from the same side of the capillary, or in a plane which intersects the incident light plane, usually at 45° in practice. In the first case the optical device is a reflector. The color cut-off filter is then situated on the path of the reflected rays, and may optionally be incorporated in the capillary tube itself. In the second case, the device may also be a filter.

Various types of reflecting material may be used for making the reflector, e.g. a foil of metal when the reflector is deposited on the surface of the capillary tube (generally made of fused silica) or a metal or a silver salt deposited by vaporization, chemical deposition, electrochemical deposition, etc. . . . , on the outside of the capillary.

The reflector may overlie a greater or lesser portion of the capillary tube, e.g. going from a semicylindrical portion to an almost complete overlying which leaves a passage for reflected light only in the observation direction. The non-reflecting portion may include a color cut-off filter.

When a vaporization technique is used for coating the capillary tube on the outside, a protective film is applied on the surface of the capillary tube that is not to be coated, with the film being removed after the portion that is to be treated has been coated.

Because of the presence of the reflector, the emitted light may be directed and/or the quantity of light picked up may be increased, thereby reducing the detection threshold.

BRIEF DESCRIPTION OF THE DRAWING

The sole FIGURE of the accompanying drawing is a diagrammatic representation of a length of a capillary tube adapted to constitute a part of the capillary electrophoresis apparatus, the tube, in accordance with the invention, including a reflector (or a filter) of the invention over a portion thereof.

DETAILED DESCRIPTION

The capillary tube 1 is provided over a portion of its outside surface in the region of the detection zone 3 with a reflector 2 which reflects the light emitted within the capillary tube outwardly thereof in an observation direction (arrow A) toward any suitable pick-up or detector device (not shown), the details of such devices and their manner of operation in sensing and evaluating light which has been emitted by the substance being analyzed and emanates from the capillary tube being well known to those skilled in the art and constituting no part of the present invention and hence requiring no description herein. The reflector may extend over a greater or lesser peripheral area of the capillary tube and there may remain only a very narrow "window" for allowing light to exit along the direction A.

The reflector may be constituted by a metal foil, e.g. of aluminum, or by a reflecting polymer cut out and fixed to the capillary tube. It may advantageously be formed by depositing metal (silver, rhodium, . . . ) by vaporization, electrodeposition, etc. . . . These deposition techniques are per se well known (see, for example, C. H. Cartwright and J. Strong, *Rev. Sci. Inst.* 2 (1931), 189 and W. C. Caldwell, *J. Appl. Phys.* 12 (1941), 779) for use in coating flat as well as curved surfaces and, mutatis mutandis, may be used for forming a reflector on the capillary tube.

In order to make a color cut-off filter, it is possible, for example, to use techniques of pyrolysis or mirror making with metal salts of different natures depending on the desired cut-off.

I claim:

1. A capillary electrophoresis apparatus adapted for use in detection by fluorescence, said apparatus including a capillary tube having a fluorescence detection zone in a length thereof; wherein the improvement comprises that said capillary tube includes an incorporated optical device in the region of said fluorescence detection zone, said optical device comprising a color cut-off filter.

2. A capillary electrophoresis apparatus adapted for use in detection by fluorescence, said apparatus including a capillary tube having a fluorescence detection zone in a length thereof; wherein the improvement comprises that said capillary tube includes an incorporated optical device in the region of said fluorescence detection zone, said optical device comprising a reflector.

3. A capillary electrophoresis apparatus according to claim 2, wherein said optical device is formed on the outside surface of said capillary tube.

4. A capillary electrophoresis apparatus according to claim 2, wherein said optical device occupies only a portion of the area of said fluorescence detection zone.

5. A capillary electrophoresis apparatus according to claim 2, wherein said reflector is formed by a metal deposited by vaporization or by electro-deposition.

6. A capillary electrophoresis apparatus according to claim 2, wherein said reflector is formed by a reflecting polymer film.

* * * * *